United States Patent
Zabara et al.

(10) Patent No.: US 6,721,603 B2
(45) Date of Patent: Apr. 13, 2004

(54) NERVE STIMULATION AS A TREATMENT FOR PAIN

(75) Inventors: Jacob Zabara, Miami Beach, FL (US); Burke T. Barrett, Houston, TX (US); Steven M. Parnis, Pearland, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 10/055,021

(22) Filed: Jan. 25, 2002

(65) Prior Publication Data

US 2003/0144709 A1 Jul. 31, 2003

(51) Int. Cl.$^7$ .................................................. A61N 1/34
(52) U.S. Cl. ......................................................... 607/46
(58) Field of Search ........................................... 607/46

(56) References Cited

U.S. PATENT DOCUMENTS

| | | | |
|---|---|---|---|
| 3,796,221 A | 3/1974 | Hagfus | 607/59 |
| 4,573,481 A | 3/1986 | Bullara | 607/118 |
| 4,702,254 A | 10/1987 | Zabara | 607/45 |
| 4,865,048 A | 9/1989 | Eckerson | 607/45 |
| 4,867,164 A | 9/1989 | Zabara | 607/45 |
| 4,979,511 A | 12/1990 | Terry, Jr. | 600/377 |
| 5,154,172 A | 10/1992 | Terry, Jr. et al. | 607/64 |
| 5,188,104 A | 2/1993 | Wernicke et al. | 607/40 |
| 5,215,086 A * | 6/1993 | Terry, Jr. et al. | 128/421 |
| 5,304,206 A | 4/1994 | Baker, Jr. et al. | 607/2 |
| 5,330,515 A | 7/1994 | Rutecki et al. | 607/46 |
| 5,540,734 A * | 7/1996 | Zabara | 607/46 |
| 5,792,187 A * | 8/1998 | Adams | 607/5 |
| 5,861,015 A * | 1/1999 | Benja-Athon | 607/46 |
| 6,208,902 B1 * | 3/2001 | Boveja | 607/46 |

* cited by examiner

Primary Examiner—Carl Layno
(74) Attorney, Agent, or Firm—Blank Rome LLP (57) ABSTRACT

A method and apparatus are disclosed for treating patients suffering from severe, unrelenting pain. A therapeutic stimulation signal is selectively applied from a stimulus generator, when activated, to at least some of plural electrodes implanted in stimulating relation to at least two nerves among the patient's trigeminal, vagus, glossopharyngeal and sympathetic nerves, and the stimulus generator is activated to generate the therapeutic stimulation signal to alleviate the pain under treatment. Alternatively, the therapeutic stimulation signal is selectively applied to at least one electrode implanted in stimulating relation to at least one of the patient's trigeminal, vagus, glossopharyngeal and sympathetic nerves, and if the selected nerve is the vagus nerve, the signal is applied to a supra-diaphragmatic or sub-diaphragmatic site, either unilaterally or bilaterally to one or both branches, respectively, of the vagus nerve.

49 Claims, 2 Drawing Sheets

NERVE STIMULATION AS A TREATMENT FOR PAIN

BACKGROUND OF THE INVENTION

The present invention relates generally to methods and apparatus for treating or controlling medical, psychiatric or neurological disorders by application of modulating electrical signals to a selected nerve or nerve bundle of a patient, and more particularly to techniques for treating pain syndromes in patients by selective electrical stimulation of at least one of the trigeminal, glossopharyngeal, vagus and sympathetic nerves.

The most commonly experienced form of pain is attributable to a stimulus on nerve endings, which transmits impulses to the cerebrum. In this nociception or nociceptive pain, a somatic sensation of pain, the organism is informed of impending tissue damage. The pain signals are initially processed by somatic and visceral free nerve endings—nociceptors. A pathway for nociceptive pain exists within the central nervous system (CNS) through neurons that are the basic excitable cell units of the nerve tissue in the CNS. Each neuron transmits impulse information about the stimulus on the nerve endings along portions of the pathway.

Other types of pain, such as neuropathic pain and psychogenic pain, may develop without actual impending tissue damage. Neuropathic pain involves a disease of the nervous system, usually from an underlying disease process or injury, typically arising after injury to elements of the nervous system involved in nociception. For example, peripheral nerve injury may occur in which the lesions de-afferent the nociceptive pathway, that is, produce a state of loss of afferent input by removal of the incoming signal fiber functions of the pathway.

The nociceptive pathway serves to protect the organism from pain, such as that experienced from a burn. This pathway is inactive unless danger to the organism exists. It begins with activation of peripheral receptors, the signal traveling up the peripheral nerve and into the spinal cord where synapses are made on second order neurons. The latter transmit the pain signal up the spinal cord in the spinothalamic tract ending in the thalamus. The prevailing view is that pain is recognized or perceived in the thalamus. Ventrolateral and ventromedial thalamic nuclei project to the cortex, where the pain is processed respecting localization and other integrative characteristics.

The neuropathic or psychogenic pain pathways are not associated with immediate action to prevent injury. For example, pain experienced following amputation of a limb is neuropathic—no danger of injury exists to the missing limb. Psychogenic pain is a chronic condition of pain without definite organic pathology.

Pain signals originate from peripheral neural receptors, the sensory nerve endings responsive to stimulation, typically from free nerve endings in the skin or the organs. When activated, a graded receptor potential is generated which causes an axon in the nerve fibers to fire action potentials. Action potentials are electrical impulses that self-propagate in a series of polarizations and depolarizations transmitted down the axon. Whether specific pain fibers exist or the sensation of pain comes from recognition of a pattern of impulses, the pain sensations are usually carried by small diameter nerve fibers. Initially, the receptor potential varies in amplitude and may dissipate rapidly with time despite a continuing stimulus, with consequent reduction in the firing frequency in the nerve fiber.

A descending pathway that can inhibit the incoming pain signals is important in the body's endogenous control of pain. It includes the periaqueductal grey, the dorsal raphe nuclei, locus ceruleus, and nuclei of the medullary reticular formation. Spontaneous activation of the pathway, which may involve activation of the endogenous opiate system, tends to suppress pain transmission.

Other projections from the periphery may also assist to gate pain, for example pain transmission is inhibited with the activation of large diameter A afferents activated by vibration, such as when the individual's hand is burned and is involuntarily shaken in response. Transcutaneous electrical nerve stimulation (TENS) analgesia also applies this technique, using a non-invasive procedure to submit electrical impulses from an external stimulator through electrodes on the skin to reduce transmission of pain signals to the brain.

Some pain syndromes are associated with an overactive sympathetic nervous system. This occurs following peripheral nerve injury, with resulting pain and sympathetic activity known as causalgia. There is evidence, for example, that norepinephrine—a transmitter of the sympathetic system—excites nociceptive fibers to produce this abnormal pain. It is possible, however, that aberrant nerve transmission results in activation of sympathetic afferents and to the overactivity.

The sensation of pain is subjective, the clinical reaction differing from patient to patient. The patient's interpretation of the sensation and its potential sources can lead to apprehension and distress that exacerbates the pain itself. Concentrations of excitatory and inhibitory neurotransmitters in the spinal cord and the brain may vary from individual to individual in response to different stimuli. This may be part of the basis for differences in the tolerance for pain among individuals, and even in the same individual over time. The tolerance for or threshold of pain is, in any case, a dynamic process that depends on the state of the organism, as, for example, instances of minimal pain being experienced for some injuries suffered by soldiers in battle.

The physician's diagnosis of the site and nature of the underlying pathology of pain depends substantially on historical information provided by the patient. This information includes location of the pain, the extent that it tends to radiate, its intensity, whether it is continual or recurring, the conditions or medications that tend to reduce or increase its severity, in addition to other factors. However, different patients describe pain and its apparent sources in different ways, and some are unable to describe it adequately as to specific site or nature. Prescribing the proper treatment requires an understanding of the underlying organic basis of the pain, and is particularly difficult with patients who experience chronic pain syndromes.

Common complaints include existence of spinal pain, usually in the cervical or lower spine, headache, facial pain, neck pain, and pain in the extremities. Chronic pain that lacks pathological basis is psychogenic, and may be symptomatic of patients suffering from tension, anxiety, depression, hysteria, hypochondria, or simply malingering. But persistent or recurring pain may be neuropathic, attributable to a condition such as arthritis, peripheral nerve pain such as causalgia, or peripheral neuropathy. Hyperpathia and hyperalgesia patients suffer excessive painful reaction to what may constitute normal pain sensations in most individuals.

Drug therapy remains the principal form of treatment for pain, including prescription of analgesics, corticosteroids, antidepressants, topical anesthetics and local anesthetic injections. In acute settings, as after surgery, it is common to prescribe narcotics and anti-inflammatory drugs. For chronic pain, anti-inflammatory drugs are generally the preferred prescription. Other drug therapies in use include tricyclic antidepressants for activating the descending pathways that provide analgesia. Local or systemic administration of anesthetic agents may be used in some cases. Opiates delivered by programmed administration to the cerebrospinal fluid by external drug pumps have been prescribed for patients with intractable pain, especially cancer patients.

TENS analgesia has been most often used for pain following peripheral nerve injury (deafferentation), or for back pain which is chronic and refractory to surgical therapy, or in other cases where surgery is not indicated. Other therapies include dorsal column stimulation and CNS stimulation. The former requires implantation of electrodes in the dorsal column of the spinal cord for activation of fibers to suppress incoming pain signals. CNS stimulation usually involves stimulation of the periaqueductal grey in the midbrain to activate descending inhibitory pathways.

In some, albeit rare situations, ablative procedures are used to control chronic pain by interrupting the afferent pain pathways. The peripheral root may be cut to block incoming fibers. The ventral lateral aspect of the cord that contains spinothalamic fibers may be lesioned. In some cases, sectioning of the cingulate gyrus may aid in controlling pain. In cases where the pain returns, lesions may continue to be made higher up the nervous system axis. It is believed that a pain engram or memory may be formed and distributed in multiple CNS sites.

It is a principal object of the present invention to provide new techniques for treatment of pain through stimulation of certain nerves. In U.S. Pat. No. 5,330,515, assigned to the assignee of the present application, pain therapy is administered by selective stimulation of the patient's vagus nerve. Pain, especially neuropathic or psychogenic pain, but also nociceptive pain where the patient is suffering from a terminal disease, is treated by application of a programmed, preferably pulse signal to the vagus nerve to excite primarily the small afferent fibers of the nerve. This is intended to activate descending anti-nociceptive pathway to inhibit the chronic or persistent pain being experienced by the patient. In that patent, the preferred but not the only site for the vagus stimulation is in the patient's neck—the cervical region—, at a point above the location of the pain felt by the patient, in the sense of a patient standing upright.

SUMMARY OF THE INVENTION

The present invention provides improvements in therapy for alleviating chronic or persistent pain, particularly neuropathic and psychogenic pain, by electrical stimulation of any one or more, or all, of the afferent fibers of the trigeminal, vagus and glossopharyngeal nerves, and of the sympathetic nerves, to modulate the electrical activity of the respective nerve or nerves, primarily to activate the descending anti-nociceptive pathway, to inhibit or mask the sensation of pain.

The trigeminal nerve is one (a pair) of the twelve pairs of cranial nerves (or cranial nerves having two branches) of the peripheral nervous system that arise from the brain and branch out from and connect the CNS to other parts of the body. The cranial nerves are also classified as part of the somatic system through which the CNS is connected to the skin and skeletal muscles, concerned with conscious activities of the organism. The trigeminal is one of the mixed nerves of the cranial nerves, with both sensory and motor fibers. It has ophthalmic, maxillary and mandibular divisions, which, as those designations imply, comprise fibers (sensory) that transmit impulses from the region of the eyes, forehead and scalp; from the upper jaw, palate and skin of the face; and from the lower jaw and related areas, respectively; and motor fibers that transmit impulses to muscles of the jaws and mouth.

The vagus nerve is also a mixed pair of the cranial nerves. Its motor fibers transmit impulses to the muscles associated with speech and swallowing, the heart, and smooth muscles of the visceral organs in the thorax and abdomen. Its sensory fibers transmit impulses from the pharynx, larynx, esophagus, and the visceral organs in the thorax and abdomen.

The glossopharyngeal nerve is also a pair among the twelve cranial nerves, and also one of the mixed nerves with both sensory and motor fibers. Its sensory fibers transmit impulses from the carotid arteries, pharynx, tonsils and posterior tongue, while its motor fibers transmit impulses to the salivary glands and the muscles of the pharynx for swallowing.

The sympathetic nerves are a section of the autonomic nervous system. The latter is part of the peripheral nervous system that functions independently and continuously without conscious effort, such as to regulate the individual's heart rate, blood pressure, body temperature and breathing rate. Sympathetic nerve fibers, like the nerve fibers of the parasympathetic division of the autonomous nervous system, are motor fibers with two neurons, the cell body of one located in the brain or spinal cord and that of the other housed in an autonomic ganglion. The axon of the former is a preganglionic fiber that leaves the CNS and forms a synapse with one or more nerve fibers of an axon of the latter, a postganglionic fiber.

To provide the therapy, a medical interventional device is implanted in the patient at a position in the chest or the abdomen selected to accommodate the patient's cosmetic desires as well as to be positioned within a region accessible to the designated nerve. The implanted device responds to activation to generate an electrical signal whose parameters are predetermined to deliver the desired therapy to the patient to alleviate or mask the pain. To that end, an electrode at the distal end of an electrical lead is implanted in stimulating and sensing relation onto the designated nerve, which may be the trigeminal, the glossopharyngeal, one of the sympathetics, or the vagus. For example, the electrode may be of a helical design or other suitable conventional design.

The implanted medical interventional device may be activated manually or automatically to deliver the therapeutic signal to the selected nerve via the implanted lead-electrode system, and the device may be programmed to deliver the signal continuously, periodically or intermittently when activated. Preferably, the signal is generated continuously by the device, in the sense of delivery according to its selected parameters, as explained further below. Alternatively, the signal is generated by activation of the device either manually or in response to a detectable symptom of pain or detectable precursor of a pain reaction. To that end, the device may incorporate or otherwise interact with an associated sensor that detects the manifestation of the pain and emits an activating signal to trigger activation of the implanted device. For example, if the patient's pain is such that it causes spasms or involuntary twitching of a muscle in a particular part of the body affected by the pain, the selected sensor is designed to detect and respond to the spasms or twitching to produce the activating signal for the device to generate its stimulating therapeutic signal.

Alternatively, the therapeutic signal may be generated by the implanted device in response to a command from the patient or attending caregiver upon recognition of the onset of a pain attack, i.e., manually, or prophylactically according to the time of day or to the patient's circadian rhythm. To allow patient activation, the device is designed to respond to a signal derived from an external source. For example, the patient may perform manual activation whenever pain is perceived, by externally positioning a magnet adjacent the implanted device to operate a reed switch in the device. Other means that may be utilized for patient activation of the implanted device are described in U.S. Pat. No. 5,304,206 to R. G. Baker, Jr. et al. (referred to herein as "the '206 patent"), which is assigned to the same assignee as the present application. Prophylactic activation is desirable in cases where the patient tends to suffer pain at a certain part of the day, such as arthritic pain in the early evening or early morning. In such a case, the device includes a clock by which a timing signal is emitted for activation at a programmed time or times during the day that the pain is generally experienced.

The therapeutic signal is preferably a pulse waveform having parameters such as pulse amplitude, output current, pulse width, pulse repetition frequency, on/off times, etc., programmed to inhibit pain pathways or receptor potentials. The pulse repetition frequency, pulse width, output current, period, stimulation rate and ON time (duration of a continuous stimulating signal) of the device are programmable. For example, the signal duration may be 30 seconds, provided to the patient with a period of once per hour, using a constant current of 2 ma, with a pulse width of 500 ms and pulse frequency of 20 Hz. But actual values are determined from the nature of the pain and the condition of the patient, as well as by a process referred to herein as spectral optimization which involves step changes in the signal parameters or at least some of them and monitoring the patient's response or reaction. Spectral optimiztion will be described in greater detail in the detailed description, below.

According to the invention, a predetermined stimulating signal is selectively applied to at least one, and preferably more or all, of the trigeminal, vagus, glossopharyngeal and sympathetic nerves (sometimes referred to herein as the selected cranial nerve(s)) of a patient suffering from pain to treat, control and relieve the symptoms of pain. The stimulating signal to be applied to the selected cranial nerve(s) of the patient is preferably generated by an implanted neurostimulator device such as a neurocybernetic prosthesis (NCP™) nerve stimulator (generator) available from Cyberonics, Inc., of Houston, Tex., the assignee of the present application. Preferably, the neurostimulator is implanted in the patient, together with appropriate lead(s) and electrode(s) for delivery of the stimulating signal to the selected cranial nerve(s). Alternatively, the signal is applied from an external neurostimulator, to a hospitalized patient. In either case, the signal may be applied continuously, periodically or intermittently, with automatic or manual activation of the generator, depending on the nature, source and symptoms of the pain.

The quality of stimulation of at least one of the designated nerves is important in achieving the desired effect of preventing or controlling the pain. The nerve should be stimulated so as to cause the brain or specific brain processes to alleviate the pain. Several variables of the stimulation need to be controlled to achieve the optimum effect of treating or controlling the pain. In addition, optimization of control of these variables must be determined for each individual patient who is to receive the treatment because of expected variability in the responses of the patients.

A variable for initial consideration is whether only one of the designated nerves should be stimulated, or more than one but less than all should be stimulated, or all of the nerves should be stimulated simultaneously, in the course of treatment of the patient. Although stimulation of all of the nerves will, in general, provide the maximum brain response and pathway activation, and thus increase the likelihood of reaching the target tissues for achieving the desired results of the therapy, it is also true that such stimulation increases the likelihood of reaching non-target tissue(s) and the consequent possibility of undesirable side-reactions. Factors such as the patient's tolerance to the stimulation, and to the implanting surgery itself, need to be considered in determining the stimulation parameters and the extent of electrode placement.

The selection of the nerve or nerves to be stimulated also requires appropriate consideration of the origin, nature and symptoms of the pain for which the treatment is intended. The trigeminal and vagus nerves generally have a broader range of function and thus are better candidates for application of the stimulating therapeutic signal. For example, the trigeminal nerve, which subserves pain, is the preferred candidate for stimulation to treat pain of central (i.e., brain) origin, whereas the vagus nerve is preferred for treating pain of peripheral origin. The relatively one-dimensional scope of the glossopharyngeal nerve offers the opportunity for more selective brain response. Both the sympathetic and vagus nerves provide an autonomic component to pain ameliorization.

BRIEF DESCRIPTION OF THE DRAWINGS

The above and other aims, objectives, aspects, features and attendant advantages of the invention will be further understood from the following detailed description of the best mode presently contemplated for practicing the invention, by reference to certain presently preferred methods and embodiments, taken in conjunction with the accompanying drawings, in which.

DETAILED DESCRIPTION OF THE BEST MODE, METHODS AND EMBODIMENTS

Before launching into a description of the best mode of practicing the invention, it will be useful to explore the subject of pain and its various forms of treatment in somewhat greater detail. Pain may accompany virtually all of the diseases with a neurological component, such as cancer, diabetes, and post-herpetic neuralgia. Although numerous analgesic drugs and other treatments are available, many patients suffer multiple episodes and develop a chronic, unremitting course of pain. For medication of refractory patients, the principal options have been surgery or stimulation or nerve block, but often even these prove to be ineffective, especially in neuropathic pain. Many refractory patients are chronically ill (with cancer, diabetes, etc.), the added burden of pain being a serious assault on the patient's quality of life and creating a great need for alternative therapies for these patients.

At the neurophysiological level, pain is thought to be based on neurotransmitters. The pathogenesis of pain is not fully understood, but studies have implicated spinothalamic and other central nervous system (CNS) pathways.

Vagus nerve stimulation has been shown to inhibit pain behavioral responses or reflexes, as well as to alter cerebral metabolism and blood flow, and to affect neurotransmitter systems involved in pain. Anatomic, physiological, biochemical, and nosologic considerations indicate that vagus nerve stimulation in humans can be effective in the treatment of refractory pain.

It is often difficult to separate the physical component from the psychological component of pain, because it is apparently the only sensation which does not have its own, clearly defined energy or receptor. Although not generally accepted today, the Gate theory of pain was probably the first clear hypothesis of pain, stating that C fibers carried pain impulses which could be blocked at the first synapse in the spinal cord by excitation of A fibers. This is analogous to relieving an itch by scratching. The Gate theory may have been the impetus for developing TENS devices and spinal cord stimulators. The pain impulses travel from a receptor on the skin to a synapse in the spinal cord, for example, then cross to the other side and continue upwards in the spinothalamic tract, where another synapse sends them to the sensory cortex (origin of the sensation of pain). Distraction from pain can give rise to analgesia such as used in the Lamaze technique of childbirth or acoustic analgesia in dentistry. Hypnosis and acupuncture have also been successful under certain conditions.

Direct stimulation of the human trigeminal nerve has been attempted for the treatment of certain types of pain in the head and face. For instance, damage of the trigeminal nerve may cause neuropathy, a pain that is continuous and described as burning, and confined to the territory of the trigeminal nerve, and extremely difficult to manage. Usually it does not respond to carbamazepine and analgesics, but sometimes responds to transcutaneous nerve stimulation, or direct stimulation of the trigeminal ganglion and rootlets. Prior to permanent electrode implantation, trial stimulation is initiated via a percutaneous electrode in the trigeminal cistern.

Since pain is a subjective response by the patient, it is difficult to develop quantitative measures of pain. However, measurement of pain associated problems, depending on the clinical cause of pain, is possible. For instance, in trigeminal nerve stimulation (TNS), thresholds to mechanical and thermal stimuli tended to increase, although the values of the intact side of the face were rarely attained. The threshold for host pain was abnormally low as compared to the normal side. As for stimulation, the threshold became normal. Similar results were observed with cold and tactile sensibility.

Stimulation of the sensory thalamus has been utilized to control pain, such as pain from postherpetic neuralgia and anesthesia dolorosa. In a few instances, patients were unable to differentiate sensations produced by thalamic stimulation from those of the trigeminal ganglion or roots stimulation.

Both spinal cord and trigeminal nerve stimulation can be accompanied by paresthesia that covers the painful area. The pulse width is critical for controlling the distribution of the paresthesia. Although the mode of action of nerve stimulation for pain is poorly understood, it appears that actuation of low threshold nerves produces inhibition, referred to as "gates".

The primary pain in trigeminal neuropathy is continuous, although paroxysmal pain occurs in rare cases. Relief is only occasionally obtained with carbamazepine. Analgesics and narcotics are ineffective. Facial postherpetic neuralgia and anesthesia dolorosa may be controlled by stimulation of the sensory thalamus, but this is not routine. Although trigeminal nerve stimulation is a simple treatment to administer, patients are often annoyed by having black rubber electrodes taped to their faces. Direct stimulation of the trigeminal nerve or ganglion and rootlets has been used as an alternative, and may improve the efficacy of stimulation (see Meyerson et al, Neurology, Vol. 18, No. 1, 1986).

It has been demonstrated that vagal afferents could inhibit spinothalamic neurons associated with cardiac pain. The antinociceptive effects of relatively small doses of morphine involve vagal afferents. It is possible that morphine activates vagal opioid receptors. Spinothalamic neurons contain a major pathway for the transmission of pain, and vagal afferent stimulation has been shown to prevent pain transmission in those neurons. Vagal stimulation could also inhibit responses to somatic activation.

The mechanism of vagus nerve stimulation effectiveness is related to projections from the nucleus tractus solitarius (NTS), where vagal afferents terminate primarily, to many different regions of the brain, including the locus coeruleus, hypothalamus, thalamus, amygdala, cerebellum, etc.). In humans, changes in blood flow have been detected in several brain structures, including the thalamus posterior temporal cortex, putamen, inferior cerebellum (Ko et al, 1996), and thalamus, posteentral gyrus, hypothalamus, insular cortex, inferior cerebellum, hippocampus, amygdala, posterior cingulate gyrus (Henry et al, 1997), indicating that vagal stimulation can change neuronal activity significantly in these structures.

Effectiveness of vagus nerve stimulation for control of neuropathic pain may be established by electrical stimulation of the trigeminal nerve or ganglion in trigeminal neuropathic pain. Although not the vagus, the trigeminal is another cranial nerve; and although not diabetic or herpetic neuropathic pain, it is trigeminal neuropathy. The mechanism by which neuropathic pain is caused is unknown, but it appears to be similar in diabetic, postherpetic and trigeminal neuropathy. The surgery involved for vagus nerve stimulation may be simpler and faster than for trigeminal nerve stimulation.

Vagus nerve stimulation can be considered in patients with pain resulting from severe nerve damage, or with spinal cord compression, where even the combined use of narcotics, non-narcotics and adjuvants that enhance analgesia either is not sufficient or provides no relief. The vagus nerve consists of A, B, and C fibers, although the vast majority are C (unmyelinated), and the A and B are mainly in the thoracic distribution (heart, lungs, etc.). The nerve has somatic and visceral afferents, i.e., inward conducting nerve fibers which convey impulses toward a nerve center such as the brain or spinal cord, and efferents, i.e., outward conducting nerve fibers which convey impulses to an effector to stimulate it and produce activity. The afferents have cell bodies in the nodose ganglion, which primarily projects to the medulla and terminate mainly in the NTS, but also in the area postrema and spinal nucleus of the trigeminal nerve. After synapsing in these regions, axonal projections are sent to a number of regions or nuclei of the brain (thalamus, amygdala, hypothalamus, hippocampus, cerebellum, etc.).

Differences between stimulation of the cervical vagus and the subdiaphragmatic vagus is to be expected since both the number of fibers and fiber composition is different in these vagal nerves. However, virtually all the neurons in the subdiaphragmatic vagus are also included in the cervical vagus, the main additional contributions to the latter being the cardiovascular and respiratory neurons which tend to be primarily A and B fibers, whereas the subdiaphragmatic vagus is primarily composed of C fibers.

Cervical vagus stimulation can either facilitate or inhibit the tail flick (rat) reflex (TF). Low intensities (between 2.5 and 20 ma, 20 Hz, 2 ms) facilitate the reflex, which is unaffected by neonatal capsaicin treatment (removing C fibers). The intensity of stimulation must be increased to over 30 ma to produce inhibition. Inhibition abruptly increases at 80% of the intensity required for complete inhibition of the TF, which indicates the emergence of the C fibers, although the facilitation at low intensities must be overcome by inhibition. Very high intensities are required (1000–2000 ma) for inhibition of TF in rats treated as neonates with capsaicin, which again points to vagal afferent C fibers as critical in inhibition of TF, as does claimed optimal stimulus parameters of 20 Hz and 2 ms.

Jaw opening (depression of the mandible) can be reflexly produced by a noxious or harmful substance in the oral cavity. For example, the presence of a cherry pit in the mouth could produce tooth fracture during forceful mastication. This reflex is similar to lifting of the foot (leg flexion) when stepping on a tack or removal of the hand (arm flexion) from a hot stove. The jaw-opening reflex is inhibited (in cats) by electrical stimulation of the cervical, thoracic, or cardiac vagus, occurring initially at a latency of 50 ms, with maximal inhibition at 200 ms. The jaw-opening reflex is truly a reflex response, and although it does not demand the existence of pain it is most often accompanied by pain.

The stimulation currents necessary to produce inhibition of TF are less for cervical vagus stimulation than for either the dorsal or the ventral branch of the subdiaphragmatic vagus. Unlike cervical vagus stimulation, the subdiaphragmatic vagus does not cause facilitation of TF. The linear increase of inhibition with current intensity indicates a steadily increasing activation of fibers, with no specific fiber groups being critical for the inhibitory effect. Thus, the facilitatory effect observed with low intensities of current in cervical vagus stimulation may be due to cardiopulmonary fibers. The cardiopulmonary afferents end in the caudal NTS, the NTS being the initial relay for vagal afferents inhibition of TF and spinothalamic nociceptive transmission and the jaw-opening reflex.

Neuropathic pain can result from a dysfunctional or damaged peripheral nervous system. If the damage is sufficiently traumatic, it results in a progressive degeneration of the axon to a certain point; then, if possible, the cell body regulates the regeneration and reinnervation by the axon. Impulses mediated by C nociceptor fibers correspond to dull or burning, poorly localized (protopathic) pain. The spinothalamic pathway of pain transmission projects to the contralateral thalamus and then to the sensory cortex. The spinoreticulothalamic pain pathway connects with the medullary and mesencephalic reticular formation, and projects to the thalamus and hypothalamus, and then to the cortex and limbic forebrain.

Although the mechanism of neuropathic pain is unknown, there are several possibilities, either acting individually or together. A damaged peripheral nerve can become spontaneously active and fire action potentials for relatively long periods of time. Mechanical irritation of chronically injured nerves can result in discharge. Changes in the nerve microenvironment, such as vasodilatation or inflammation, can be causal to pain. Changes in the receptive field of thalamus and somatosensory cortex can occur as a result of peripheral nerve injury.

Cancer pain, as might be expected, involves a wide range of painful phenomena and initiation. Bone pain is particularly important, and is present in most cancer patients. Among advanced cancer patients with pain, the pain is moderate to severe in about 50%, and very severe or excruciating in another 30%. Most patients have two or more types/etiologies of cancer pain involving 1) tumors, 2) treatment, 3) physiological or biochemical changes, and 4) chronic illness. The pain can be either acute or chronic, and caused by direct tumor involvement or after diagnostic procedures and anticancer therapies, such as surgery, chemotherapy or radiation.

Tumor invasion of bone is the most common cause of pain in cancer patients. The pain is constant, but increasingly severe, and may be caused by decreasing the threshold of peripheral nociceptors, or by persistent nociceptor stimulation. The second most frequent cause of cancer pain is tumor compression or infiltration of peripheral nerves. This pain may result from metastatic fracture adjacent to nerves, inflammation, tumor enlargement compressing or infiltrating nerves, and is also referred to as a deafferentation pain. The abnormal sensory input, resulting from these causes, produces pathophysiologic changes in the spinal cord or brain (it is believed) and is most likely to develop when the tumor severely damages or destroys the nerves (deafferentation pain). Some of these patients respond well to sympathetic interruption.

Diffuse headache is a common result of cerebral metastasis which may result from carcinoma of the lung, breast melanoma or anal and testicular cancer. The headache is apparently caused by tumorous distension, compression or infiltration of meninges, intracranial sinus or meningeal arteries. Also, infiltration into stomach, intestine, liver, pancreas, blood vessels, etc. can cause intense pain.

Pain can occur as a consequence of thoracotomy, chemotherapy (steroids, etc.), immunosuppressive drugs (resulting in herpes zoster, etc.), or radiation therapy. For instance, for up to 20 years following radiation therapy, radiation-induced peripheral nerve tumors can develop, producing intense pain. The impact goes beyond the direct pain and affects the psychological and emotional life of the patient and family.

Cancer patients have greater anxiety and depression than patients with non-malignant pain. It seems that the diagnosis of disease is associated with a sense of helplessness and an inability to be effective, causing anxiety and fear, which are increased by the pain. Thus, personality factors are distorted by cancer pain, and relief of the pain may result in personality improvement. In addition, patients with pain appear to respond less well to treatment and die sooner (due to emotional disturbances).

Patients with cancer pain also have significantly increased levels of depression, anxiety and hostility than the cancer patient without pain. The suggestion is that designing specific therapies that target these and each component of pain, direct and indirect, is essential for the treatment of pain secondary to cancer. Although pain is supposed to be a viable sign of tissue trauma or damage, in the pain of incurable cancer, it degenerates to become a part of the problem, causing considerable psychological trauma.

Advanced cancer pain is treated primarily by systemic analgesics in combination with other drugs, which include aspirin, anti-inflammatory drugs, opioid agonists, corticosteroids, tricyclic antidepressants, anxiolytic agents, phenothiazines, etc. Aspirin and other nonopioid analgesics can relieve moderate cancer pain, and even severe pain caused by bone metastases, and may be potent prostaglandin synthetase inhibitors. However, they must be given usually at regular intervals to sustain effective analgesia, so that increase of the dose beyond a certain level does not produce additional analgesia, and they do produce adverse side effects. In addition, aspirin may lower the available concentration of a second drug by displacing it from plasma protein, but the combined use of non-narcotic and narcotic analgesics can produce additive analgesia. Adjuvant drugs include steroids, tricyclic anti-depressants, anxiolytics, phenothiazines, anticonvulsants and amphetamines.

Morphine and other potent narcotic analgesics are the most frequently used drugs for the relief of moderate to extremely severe cancer pain, and this relief can last up to 5 hours after a single dose. Methadone has a longer half-life and an analgesia lasting up to 8 hours (as does levorphanol). However, methadone and levorphanol accumulate in plasma, and may thus produce serious side effects. The side effects of these narcotics are: 1) constipation (the most frequent side effect), 2) suppression of coughing (beneficial in some patients), 3) excessive sedation, 4) drowsiness, 5) confusion, 6) dizziness, 7) nausea and vomiting, and 6) respiratory depression.

Respiratory depression can occur when a potent narcotic is administered too frequently or given in excessive doses; however, pain is a powerful respiratory stimulant and tends to counteract the narcotic-induced depression. Nonetheless, respiratory depression or even arrest can occur in patients when the pain is abruptly terminated (and its respiratory stimulating effects).

Cancer pain can be relieved by local anesthetic blocks for hours or days, and be combined with a corticosteroid, for longer effectiveness (by decreasing the nerve swelling). Cervicothoracic sympathetic block relieves the burning pain in certain types of cancer of the head, neck and chest. Side effects include arterial hypotension, toxic reactions, spinal block, and pneumothorax (accidental needle insertion in the lung). Regional anesthesia with intraspinal opioids (can bind to opiate receptors in the central terminals of peripheral nerves) impairs transmission of nociceptive information, but may produce respiratory depression. Neurolytic blocks (injection of alcohol or phenol) can destroy nerves. For instance, alcohol block of the gasserian ganglion produces pain relief in 80% of patients with advanced cancer pain in the anterior two-thirds of the head. Neurosurgical techniques, such as spinothalamic tractotomy, percutaneous cordotomy (radiofrequency lesion), commisurotomy, or cranial stereotaxic operations relieve pain in advanced cancer.

The general approach is that when the combination of non-narcotic and weak narcotic analgesics no longer controls cancer pain, the patient is given narcotic analgesics. Vagus nerve stimulation might be considered before or after narcotic analgesics, depending on the pain and the patient's circumstances, which include the intensity and duration of the pain, the physical, nutritional and mental status of the patient, the side effect's of the drug treatment. The general rule is that an effective dose of the drug be given at fixed intervals to produce continuous pain relief, which may more conveniently and rigorously be accomplished with vagal stimulation. For instance, narcotic medication should be administered at fixed intervals on an around-the-clock basis, which includes awakening the patient at night, and closely monitoring for pain relief as well as constipation, nausea, vomiting, excessive sedation, drowsiness and dizziness.

Dorsal column stimulation and direct stimulation of peripheral nerves have similar profiles of effectiveness, potentially inferior to the long-lasting effect of vagus nerve stimulation but it depends on optimizing stimulation parameters. The main issue is the possible effectiveness of the latter stimulation in relieving extremely severe pain, in which the other two types of stimulation are relatively ineffective.

Deep brain stimulation is used with some success in the management of pain in patients with advanced cancer. An electrode, with an induction receiver and external transmitter, is inserted into the internal capsule, thalamus, or hypothalamus and allows self-stimulation (the periaqueductal or periventricular gray can also be utilized). Most of the patients derived from 50% to 75% relief, but in only a few cases was the relief complete. Deep brain stimulation is ineffective in deafferentation pain, and is most effective in other pain of peripheral origin (nociceptive). Thus, TENS, direct peripheral nerve stimulation, and deep brain stimulation are all effective to some extent in pain management, but with great variability in effectiveness and with unknown mechanism of action. It appears that the elicitation of action potentials in afferent neurons, whether peripherally or centrally, can relieve pain, and when the mechanism is better understood it may be possible to increase effectiveness of stimulation techniques.

Diabetic neuropathy apparently involves a progressive, destructive change in peripheral nerve, especially a sensory polyneuropathy, which is the most frequent form of peripheral nerve disorder in diabetes. There is a progressive temporal pattern with the earliest sensory involvement affecting the toes. The most common symptoms are sensations of numbness and tingling. Pain can be present even when only slight abnormalities are exhibited on examination, such as aching in the feet and legs.

Nerve deterioration may occur, predominately involving loss of small fibers (C fibers). Some cases begin with a precipitous and profound loss of weight followed by severe, burning pain in the lower limbs, and hyperalgesia in which contact is very unpleasant. Serious foot ulceration is primarily related to tissue damage of which the patient is unaware because of loss of pain and temperature sensation.

Patients with diabetic neuropathy can have serious pain problems, and this can be complicated by depression. Management is first to control neuropathy by glycemic control, second to treat the pain, and third to treat depression. Vagus nerve stimulation should be considered in the treatment of the neuropathic pain, and may be of benefit in depression, with some possibility of benefit in glycemic control. Simple analgesics are of little benefit when pain is severe. Potent analgesics are not used because of the risk of addiction.

An assumption or observation utilized in stimulation control of pain is that stimulation of sensory nerves somehow suppresses pain sensations originating from the same area (further developed as the gate theory of pain). Obviously, this is not applicable in general to vagus nerve stimulation, unless vagal nerves become neuropathic, which is a possibility in diabetic neuropathy or cancer pain.

Post-herpetic neuralgia (PHN) is the pain persisting after onset of the rash, but PHN tends to diminish in severity with time. There can be both an ongoing pain (burning, raw, aching, or tearing) and a superimposed paroxysmal pain (stabbing or electric shock-like) which commonly becomes concentrated in one part of the affected dermatome, and is accompanied frequently by an unpleasant sensitivity of the skin. Evoked sensations may be the most unbearable part of PHN, usually produced by clothing or skin stretching, and there is often associated depression.

Systemic corticosteroids and Acyclovir have been advocated in prevention, and sympathetic blockade may reduce PHN. Treatment of PHN with antidepressants (tricyclic and others) improves symptoms in about half of the patients, with better outcome related to early treatment. Capsaicin or analgesics may be tried in refractory cases.

The vagus nerve is autonomic of the parasympathetic division with many "antagonistic" functions towards the sympathetic division, and composed of approximately 90,000 neurons where about 80% are afferent and about 20% are efferent. The vagus nerve monitors and modulates the functions of internal organs, including their vital functions, and contains sensory fibers to the ear and motor fibers to the larynx. The recurrent laryngeal nerve innervates the vocal cords.

According to the present invention, after selecting the nerve or nerves on which the electrode(s) will be implanted, it is necessary to determine the site at which the electrode(s) should be placed for initiating the stimulation signal. In a preferred embodiment and method, more than one of the designated nerves among the vagus, trigeminal, glossopharyngeal, and sympathetic nerves are selected to receive the stimulating signal. It should be noted that although the terms "stimulating signal", "stimulation signal", therapeutic stimulating signal" and the like are used herein to describe the electrical signal by which the desired therapy or therapeutic regimen is delivered to the selected cranial nerve(s), the response is perhaps better understood to be a modulation of the electrical activity of the nerve(s) which can stimulate or inhibit the tissue at the nerve endings.

Figures 1, 2:
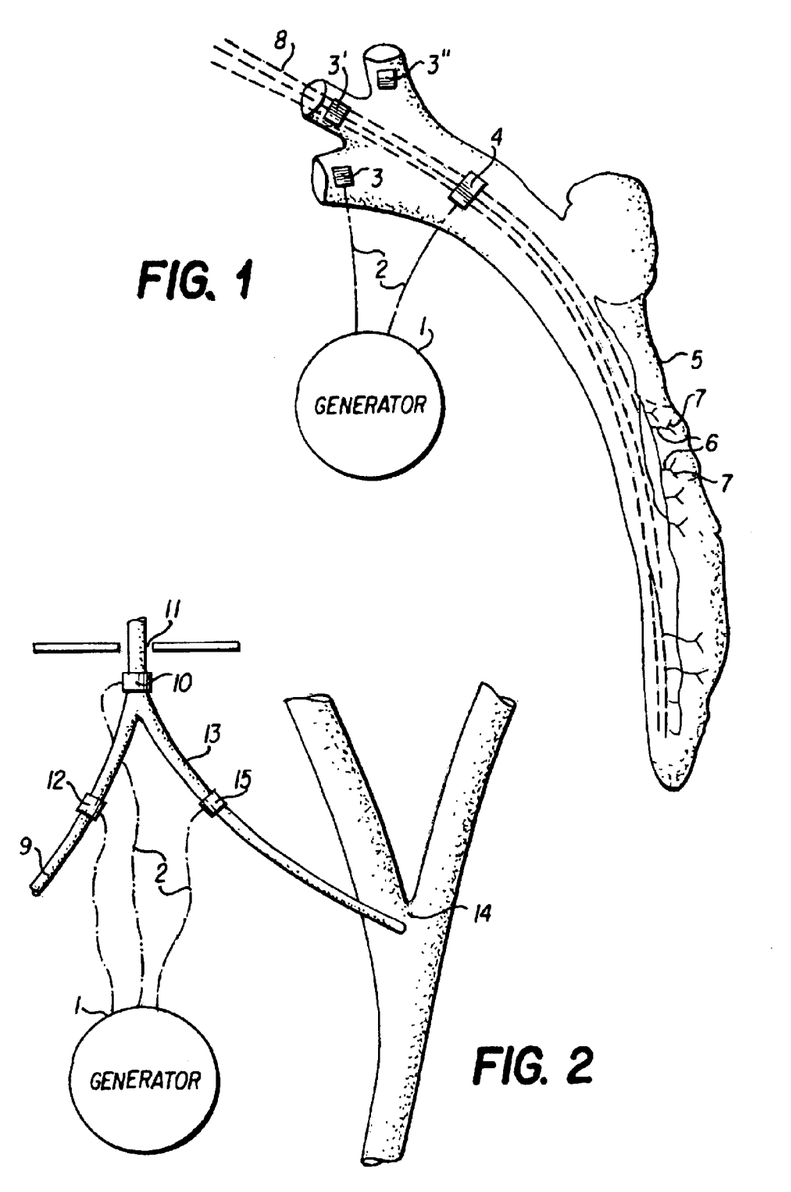
FIG. 1 is a highly simplified, schematic diagram of the trigeminal nerve, showing possible sites of electrode attachment, and coupling to the implanted stimulus generator.
FIG. 2 is a highly simplified, schematic diagram of the glossopharyngeal nerve, showing possible sites of electrode attachment, and coupling to the implanted stimulus generator.

FIG. 1 is a schematic illustration showing possible sites for attachment of electrodes to the trigeminal nerve. Stimulus generator 1 is surgically implanted at an appropriate site in the patient's body in a known manner, typically in a pocket formed just below the epidermal layer, and preferably in or near the patient's chest. One or more conventional leads 2 electrically connected to generator 1 terminate at one or more electrodes, preferably helical electrodes. The electrodes and associated leads are implanted in stimulating relation to the trigeminal nerve 8, shown as having three nerve roots. Recommended sites for electrode placement are shown at 3, 3' and 3", which are the three nerve roots of the trigeminal nerve. Another recommended site is the Gasserian ganglion 4, which is a terminus of the three roots. The medullary region 5 of the brain is also shown schematically in FIG. 1, with primary nerve endings 6 of the trigeminal nerve, and with pathway projections 7 in the brain leading away from the nerve endings 6.

Therapeutic stimulating signals travel from the site of the electrode(s) at which the signals are delivered to the nerve to the trigeminal nucleus, and then generate impulses in pathways projecting to other areas of the brain.

FIG. 2 is a schematic illustration showing possible sites for attachment of electrodes to the glossopharyngeal nerve. The references to generator 1 and associated lead(s) 2 in connection with the description of FIG. 1 apply here as well. The leads 2 terminate at one or more electrodes that are implanted in stimulating relation to on the glossopharyngeal nerve 9. A preferred site for electrode placement is site 10, just prior to where the glossopharyngeal nerve enters the brain through the jugular foramen 11. Alternatively or additionally, an electrode may be implanted at one of the branches of the glossopharyngeal nerve such as at site 12. Another branch of the nerve runs along the carotid sinus 13, which connects to the bifurcation of the carotid artery 14. It may be convenient for the surgeon to locate an electrode at site 15 on the carotid sinus by first locating the bifurcation of the carotid artery 14 and at that point identify the carotid sinus nerve which is traceable to the jugular foramen.

Figure 3:
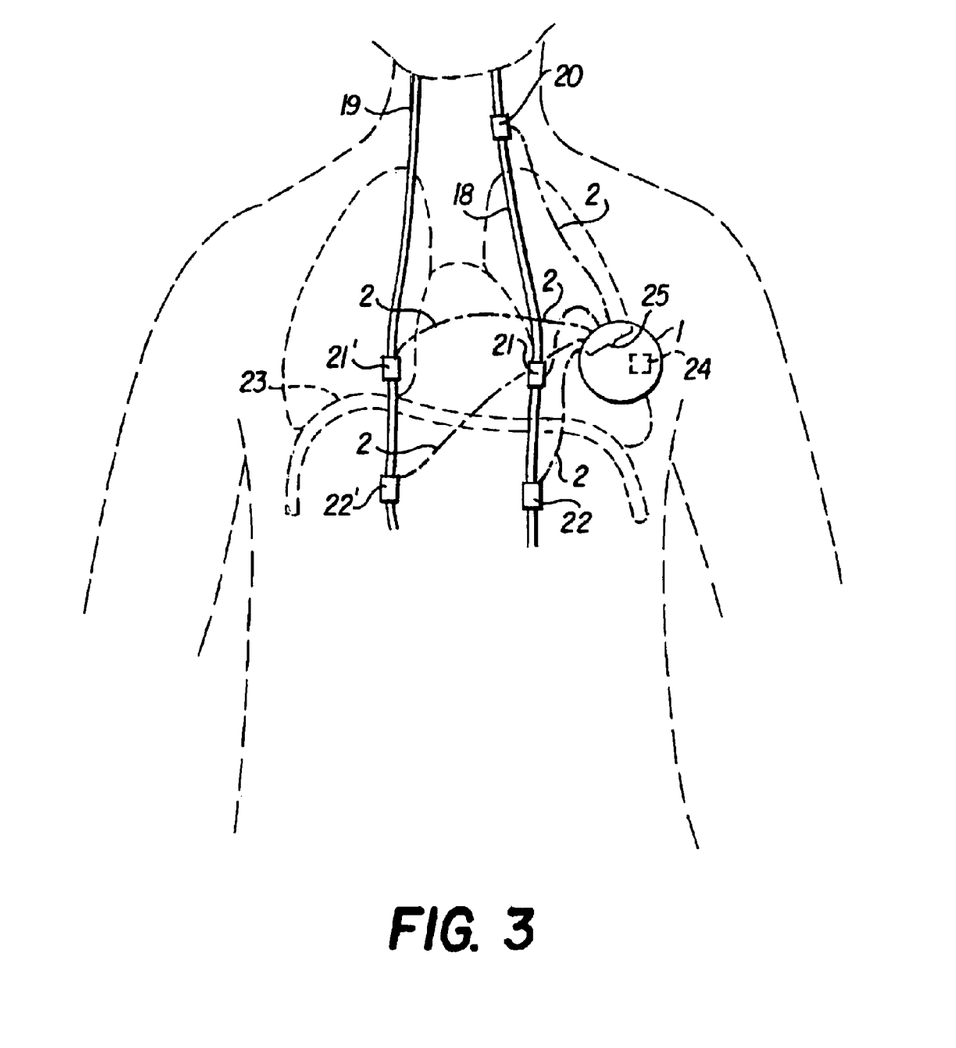
FIG. 3 is a highly simplified, schematic diagram of the vagus nerve, showing possible sites for electrode attachment, and coupling to the implanted stimulus generator.

As shown in FIG. 3, is a schematic illustration showing preferred sites for attachment of electrodes to the vagus nerve from leads 2 electrically connected to stimulus generator 1. These sites include the cervical region 20, and the supra- or sub-diaphragmatic regions 21, 22, respectively, of the vagus. The easiest surgery is performed at the cervical site, but it may be desirable for some pain sites to implant one or more electrodes at the supra- or subdiaphragmatic sites, either unilaterally or bilaterally (latter shown at sites 21' and/or 22' as well as unilateral sites 21 and/or 22, respectively). The majority of vagal afferents terminate in the nucleus of the tractus solitarius, but a vagal branch innervates the caudal nucleus of the trigeminal nerve which receives trigeminal pain afferents. Accordingly, vagal and trigeminal signals may reinforce each other for the treatment of pain.

After the selected nerve or nerves have been fitted with electrodes, and the respective lead(s) are connected to the implanted (or external) stimulus generator, it is necessary to program the generator to produce the desired stimulation therapy regimen, if the programming has not already been accomplished before or after implantation of the generator. In practice, the stimulation signal is preferably an electrical pulse signal. Using the Cyberonics NCP device as a suitable pulse generator and associated software, it is possible to program the stimulation signal parameters including its current, frequency, pulse width, period, duration and rate. As used in this specification, the parameter current refers to the number of milliamperes (ma) delivered in the signal, the parameter frequency refers to the number of cycles per second (Hz) of the current, the parameter pulse width refers to the length of time (e.g., in milliseconds) occupied by a single pulse of the signal, the parameter period refers to how often a continuous stimulation signal is applied to the electrode(s), the parameter duration refers to the length of time occupied by a single continuous stimulation delivered by the signal, and the parameter rate refers to the number of pulses applied to the electrode(s) every second to provide a single continuous stimulation.

For example, the current may range from about 0.1 to about 40 ma, but is preferably selected to have a value of from about 0.5 to about 20 ma; the frequency may range from about 0.25 to about 1000 Hz, but is preferably selected to lie in a range from about 1 Hz to about 50 Hz; the pulse width may be set in a range from about 0.05 ms to about 2.0 ms; the period might be selected for delivery of a continuous stimulation signal once a minute, or twice an hour, or other appropriate period; the duration of the stimulating signal might be selected to last 10 seconds, 30 seconds, or other appropriate duration; and the rate determined by the settings of the other parameters. Thus, a suitable therapeutic pulse signal regimen might be programmed to have a duration of 30 seconds, a period of once per hour, a constant current of 2 ma, with a pulse width of 500 ms and a frequency of 20 Hz. It will be understood, however, that the optimum value of the parameters of the stimulating signal will depend on factors such as the nature of the pain being treated and the condition of the patient.

Optimization of the stimulating signal parameters may be achieved by achieved by a process of what will be termed herein as spectral optimization. According to this process, the various parameters, or specific parameters, of the signal are increased in steps from a designated minimum value or starting value over intervals of several days or weeks, and the patient's response is monitored. The desire, of course, is to achieve a condition in which the pain is alleviated and no discomfort attributable to the stimulation signal is experienced by the patient. If discomfort occurs, no further increase in current, pulse width, frequency, and so forth, is attempted, until the discomfort response habituates. If the discomfort does not habituate, the parameters which have been increased are decreased in steps of similar period and the patient's response is monitored accordingly. Programming, both initial and changes, is accomplished by the attending physician or other caregiver in a conventional manner, using an external programmer unit with a programming wand that is placed over the implant site of the microprocessor-based stimulus generator.

As noted earlier herein, certain techniques of manual and automatic activation of implantable medical devices are disclosed in the '206 patent. For example, manual activation or deactivation of the stimulus generator can be achieved using a sensor such as an accelerometer or a piezoelectric element mounted to the inner surface of the generator can so as to detect light taps by the patient on the implant site of the generator in the patient's body. This gives the patient limited but convenient control over the device operation, to an extent which can be determined and circumscribed by the attending physician or other appropriate caregiver. It is more amenable to control that can be exercised by the patient, than other means more commonly used in prior art arrangements, such as an external magnet.

The implanted device may be programmed for some patients to undergo stimulation according to the time of day (e.g., differently during daytime and nighttime hours), or otherwise according to the circadian rhythm of the patient. This implementation is achieved in part through the incorporation of a conventional clock beyond the clocking provided for operation of the electronics package of the device.

In an exemplary embodiment of the invention, apparatus for treating patients suffering from chronic or persistent pain includes an implantable stimulus generator 1 for selectively applying, when activated, a therapeutic stimulation signal to at least some electrodes of plural leads electrically coupled to the stimulus generator. The generator includes plural receptacles, e.g., 25, FIG. 3, for receiving the plural leads 2. The plural electrodes are adapted to be implanted in stimulating relation to at least two nerves among the patient's trigeminal, vagus, glossopharyngeal and sympathetic nerves. Means are provided for activating the stimulus generator to alleviate the pain under treatment. The activating means may comprise a sensor associated with the stimulus generator (e.g., within the generator 1 case or can as at 4 (FIG. 3), or implantable independently of the generator) for detecting a predetermined action initiated by the patient, and for thereupon delivering an activation signal to the stimulus generator. As noted above, such action may be the wielding of a magnet into proximity to the site at which the stimulus generator is implanted, or tapping by the patient in proximity to that site. Or the sensor may be constructed and adapted to detect a detectable manifestation of pain experienced by the patient, to automatically issue the activation signal to the generator. Alternatively, the sensor may comprise a clock for activation according to the patient's circadian cycle.

Although a best mode of practicing the invention has been described herein with reference to certain preferred embodiments and methods of treating pain, it will be understood by those skilled in the field from a consideration of the foregoing disclosure, that variations and modifications of the described embodiments and methods may be made without departing from the true spirit and scope of the invention. Accordingly, it is intended that the invention shall be limited only to the extent required by the appended claims and the rules and principles of applicable law.

What is claimed is:

1. A method of treating patients suffering from chronic or persistent pain of neuropathic, psychogenic or nociceptive origin or causation, comprising the steps of:
selectively applying a therapeutic stimulation signal from a stimulus generator, when activated, to at least some of plural electrodes implanted in stimulating relation to at least two nerves among the patient's trigeminal, vagus, glossopharyngeal and sympathetic nerves, and activating the stimulus generator to generate said therapeutic stimulation signal to alleviate the pain under treatment.

2. The method of claim 1, wherein:
the therapeutic stimulation signal is an electrical pulse signal.

3. The method of claim 2, including:
programming parameters of the stimulation signal, including at least some of current, pulse width, pulse frequency, and duration, period and rate of stimulation, according to the nature of the pain under treatment and the condition of the patient receiving the treatment.

4. The method of claim 1, including:
selectively applying the therapeutic stimulation signal to the patient's trigeminal and vagus nerves only.

5. The method of claim 4, including:
selecting the stimulation site for the vagus nerve to be at least one of the cervical, supra-diaphragmatic and sub-diaphragmatic regions, and for unilateral or bilateral stimulation.

6. The method of claim 4, including:
selecting the stimulation site for the trigeminal nerve to be at least one of the three nerve roots or the Gasserian ganglion.

7. The method of claim 1, including:
adapting the stimulus generator for manual activation by the patient.

8. The method of claim 1, including:
adapting the stimulus generator for automatic activation in response to sensing a detectable manifestation of pain.

9. The method of claim 1, including:
adapting the stimulus generator for prophylactic activation according to the patient's circadian rhythm.

10. The method of claim 1, including:
selecting the stimulation site for the vagus nerve to be at least one of the cervical, supra-diaphragmatic and sub-diaphragmatic regions, and for unilateral or bilateral stimulation.

11. The method of claim 1, including:
selecting the stimulation site for the trigeminal nerve to be at least one of the three nerve roots or the Gasserian ganglion.

12. The method of claim 1, including:
selecting the stimulation site for the glossopharyngeal nerve to be the proximal jugular foremen just before the nerve enters the brain, or the carotid sinus branch running along the carotid sinus that connects to the bifurcation of the carotid artery.

13. The method of claim 1, including:
adapting the stimulus generator to generate the therapeutic stimulation signal continuously.

14. The method of claim 1, including:
adapting the stimulus generator to generate the therapeutic stimulation signal periodically.

15. The method of claim 1, including:
adapting the stimulus generator to generate the therapeutic stimulation signal intermittently.

16. A method of treating patients suffering from chronic or persistent pain of neuropathic, psychogenic or nociceptive origin or causation, comprising the steps of:
selectively applying a therapeutic stimulation signal from a stimulus generator, when activated, to one or more electrodes implanted in stimulating relation to the patient's trigeminal nerve, and
activating the stimulus generator to generate said therapeutic stimulation signal to alleviate the pain under treatment.

17. The method of claim 16, including:
selecting the stimulation site for electrode placement to be at least one of the three nerve roots or the Gasserian ganglion of the trigeminal nerve.

18. The method of claim 16, wherein:
the therapeutic stimulation signal is a pulse signal.

19. The method of claim 18, including:
programming parameters of the stimulation signal, including at least some of current, pulse width, pulse frequency, and duration, period and rate of stimulation, according to the nature of the pain under treatment and the condition of the patient receiving the treatment.

20. The method of claim 16, including:
adapting the stimulus generator for manual activation by the patient.

21. The method of claim 16, including:
adapting the stimulus generator for automatic activation in response to sensing a detectable manifestation of pain.

22. The method of claim 16, including:
adapting the stimulus generator for prophylactic activation according to the patient's circadian rhythm.

23. A method of treating patients suffering from chronic or persistent pain of neuropathic, psychogenic or nociceptive origin or causation, comprising the steps of:
selectively applying a therapeutic stimulation signal from a stimulus generator, when activated, to one or more electrodes implanted in stimulating relation to the patient's glossopharyngeal nerve, and activating the stimulus generator to generate said therapeutic stimulation signal to alleviate the pain under treatment.

24. The method of claim 23, including:
selecting the stimulation site for electrode placement to be the proximal jugular foramen just before the nerve enters the brain, or the carotid sinus branch running along the carotid sinus that connects to the bifurcation of the carotid artery.

25. The method of claim 23, wherein:
the therapeutic stimulation signal is a pulse signal.

26. The method of claim 25, including:
programming parameters of the stimulation signal, including at least some of current, pulse width, pulse frequency, and duration, period and rate of stimulation, according to the nature of the pain under treatment and the condition of the patient receiving the treatment.

27. The method of claim 23, including:
adapting the stimulus generator for manual activation by the patient.

28. The method of claim 23, including:
adapting the stimulus generator for automatic activation in response to sensing a detectable manifestation of pain.

29. The method of claim 23, including:
adapting the stimulus generator for prophylactic activation according to the patient's circadian rhythm.

30. A method of treating patients suffering from chronic or persistent pain of neuropathic, psychogenic or nociceptive origin or causation, comprising the steps of:
selectively applying a therapeutic stimulation signal from a stimulus generator, when activated, to at least one electrode implanted in stimulating relation to the patient's vagus nerve at one of a supra-diaphragmatic or a sub-diaphragmatic site, and
activating the stimulus generator to generate said therapeutic stimulation signal to alleviate the pain under treatment.

31. The method of claim 30, including:
selectively applying said therapeutic stimulation signal unilaterally at the supra-diaphragmatic or a sub-diaphragmatic site.

32. The method of claim 30, including:
selectively applying said therapeutic stimulation signal bilaterally at the supra-diaphragmatic or a sub-diaphragmatic site.

33. Apparatus for treating patients suffering from chronic or persistent pain of neuropathic, psychogenic or nociceptive origin or causation, comprising:
an implantable stimulus generator for selectively applying, when activated, a therapeutic stimulation signal to at least some electrodes of plural leads electrically coupled to said stimulus generator, including plural receptacles of said generator for receiving said plural leads, said plural electrodes adapted to be implanted in stimulating relation to at least two nerves among the patient's trigeminal, vagus, glossopharyngeal and sympathetic nerves, and
means for activating the stimulus generator to generate said therapeutic stimulation signal for application to implanted ones of the plural electrodes to alleviate the pain under treatment.

34. The apparatus of claim 33, wherein:
said activating means comprises a sensor associated with the stimulus generator for detecting a predetermined action initiated by the patient.

35. The apparatus of claim 34, wherein:
said sensor is responsive to a magnet wielded by the patient into proximity to the site at which flue stimulus generator is implanted.

36. The apparatus of claim 34, wherein;
said sensor is responsive to tapping by the patient in proximity to the site at which the stimulus generator is implanted.

37. The apparatus of claim 33, wherein:
said activating means comprises a sensor associated with the stimulus generator for detecting a detectable manifestation of pain experienced by the patient.

38. The apparatus of claim 33, wherein:
said activating means comprises a clock for activation according to circadian cycle.

39. A method of treating patients suffering from chronic or persistent pain, comprising the steps of:
selectively applying a therapeutic stimulation signal from a stimulus generator, when activated, to plural electrodes implanted in stimulating relation to the patient's trigeminal and vagus nerves only, and
activating the stimulus generator to generate said therapeutic stimulation signal to alleviate the pain under treatment.

40. The method of claim 39, including:
selecting the stimulation site for the vagus nerve to be at least one of the cervical, supra-diaphragmatic and sub-diaphragmatic regions, and for unilateral or bilateral stimulation.

41. The method of claim 39, including:
selecting the stimulation site for the trigerminal nerve to be at least one of the three nerve roots or the Gasserian ganglion.

42. A method of treating patients suffering from chronic or persistent pain, comprising the steps of:
selectively applying a therapeutic stimulation signal from a stimulus generator, when activated, to at least some of plural electrodes implanted in stimulating relation to at least two nerves among the patient's trigeminal, vagus, glossopharyngeal and sympathetic nerves, and activating the stimulus generator to generate said therapeutic stimulation signal to alleviate the pain under treatment, and
further including adapting the stimulus generator for prophylactic activation according to the patient's circadian rhythm.

43. A method of treating patients suffering from chronic or persistent pain, comprising the steps of:
selectively applying a therapeutic stimulation signal from a stimulus generator, when activated, to at least some of plural electrodes implanted in stimulating relation to at least two nerves among the patient's trigeminal, vagus, glossopharyngeal and sympathetic nerves, and
activating the stimulus generator to generate said therapeutic stimulation signal to alleviate the pain under treatment, and
further including selecting the stimulation site for the vagus nerve to be at least one of the cervical, supra-diaphragmatic and sub-diaphragmatic regions, and for unilateral or bilateral stimulation.

44. A method of treating patients suffering from chronic or persistent pain, comprising the steps of:
selectively applying a therapeutic stimulation signal from a stimulus generator, when activated, to at least some of plural electrodes implanted in stimulating relation to at least two nerves among the patient's trigeminal, vagus, glossopharyngeal and sympathetic nerves, and activating the stimulus generator to generate said therapeutic stimulation signal to alleviate the pain under treatment, and further including adapting the stimulus generator to generate the therapeutic stimulation signal continuously.

45. A method of treating patients suffering from chronic or persistent pain, comprising the steps of;

selectively applying a therapeutic stimulation signal from a stimulus generator, when activated, to one or more electrodes implanted in stimulating relation to the patient's trigeminal nerve, and activating the stimulus generator to generate said therapeutic stimulation signal to alleviate the pain under treatment, and further including adapting the stimulus generator for prophylactic activation according to the patient's circadian rhythm.

46. A meted of treating patients suffering from chronic or persistent pain, comprising the steps of:

selectively applying a therapeutic stimulation signal from a stimulus generator, when activated, to one or more electrodes implanted in stimulating relation to the patient's glossopharyngeal nerve, and activating the stimulus generator to generate said therapeutic stimulation signal to alleviate the pain under treatment, and further including adapting the stimulus generator for prophylactic activation according to the patient's circadian rhythm.

47. Apparatus for treating patients suffering from chronic Or persistent pain, comprising:

an implantable stimulus generator for selectively applying, when activated, a therapeutic stimulation signal to at least some electrodes of plural leads electrically coupled to said stimulus generator, including plural receptacles of said generator for receiving said plural leads, said plural electrodes adapted to be implanted in stimulating relation to at least two nerves among the patient's trigeminal, vagus, glossopharyngeal and sympathetic nerves, and means for activating the stimulus generator to generate said therapeutic stimulation signal for application to implanted ones of the plural electrodes to alleviate the pain under treatment, wherein said activating means comprises a sensor associated with the stimulus generator for detecting a predetermined action initiated by the patient.

48. Apparatus for treating patients suffering from chronic or persistent pain, comprising:

an implantable stimulus generator for selectively applying, when activated, a therapeutic stimulation signal to at least some electrodes of plural leads electrically coupled to said stimulus generator, including plural receptacles of said generator for receiving said plural leads, said plural electrodes adapted to be implanted in stimulating relation to at least two nerves among the patient's trigeminal, vagus, glossopharyngeal and sympathetic nerves, and means for activating the stimulus generator to generate said therapeutic stimulation signal for application to implanted ones of the plural electrodes to alleviate the pain under treatment, wherein said sensor is responsive to a magnet wielded by the patient into proximity to the site at which the stimulus generator is implanted.

49. Apparatus for treating patients suffering from chronic or persistent pain, comprising:

an implantable stimulus generator for selectively applying, when activated, a therapeutic stimulation signal to at least some electrodes of plural leads electrically coupled to said stimulus generator, including plural receptacles of said generator for receiving said plural leads, said plural electrodes adapted to be implanted in stimulating relation to at least two nerves among the patient's trigeminal, vagus, glossopharyngeal and sympathetic nerves, and means for activating the stimulus generator to generate said therapeutic stimulation signal for application to implanted ones of the plural electrodes to alleviate the pain under treatment, wherein said sensor is responsive to tapping by the patient in proximity to the site at which the stimulus generator is implanted.

* * * * *